(12) United States Patent
Jolly et al.

(10) Patent No.: US 9,572,974 B2
(45) Date of Patent: Feb. 21, 2017

(54) ATRAUMATIC MODIOLAR HUGGING ELECTRODE

(71) Applicant: MED-EL Elektromedizinische Geraete GmbH, Innsbruck (AT)

(72) Inventors: Claude Jolly, Innsbruck (AT); Anandhan Dhanasingh, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 509 days.

(21) Appl. No.: 14/245,038

(22) Filed: Apr. 4, 2014

(65) Prior Publication Data

US 2014/0303548 A1   Oct. 9, 2014

Related U.S. Application Data

(60) Provisional application No. 61/808,655, filed on Apr. 5, 2013.

(51) Int. Cl.
*A61N 1/05* (2006.01)

(52) U.S. Cl.
CPC .................. *A61N 1/0541* (2013.01)

(58) Field of Classification Search
None
See application file for complete search history.

(56) References Cited

U.S. PATENT DOCUMENTS

| | | | |
|---|---|---|---|
| 5,653,742 A * | 8/1997 | Parker | A61D 7/00 607/116 |
| 6,038,484 A | 3/2000 | Kuzma | |
| 6,125,302 A * | 9/2000 | Kuzma | A61N 1/0541 607/137 |
| 6,266,568 B1 * | 7/2001 | Mann | A61N 1/0541 607/137 |
| 6,304,787 B1 | 10/2001 | Kuzma et al. | |
| 6,374,143 B1 * | 4/2002 | Berrang | A61N 1/056 607/122 |
| 6,397,110 B1 * | 5/2002 | Kuzma | A61N 1/0587 128/897 |
| 6,421,569 B1 | 7/2002 | Treaba et al. | |

(Continued)

OTHER PUBLICATIONS

International Searching Authority, Authorized Officer Blaine R. Copenheaver, International Search Report and Written Opinion,—PCT/US2014/032912, date of mailing Sep. 4, 2014, 11 pages.

*Primary Examiner* — Brian T Gedeon
(74) *Attorney, Agent, or Firm* — Sunstein Kann Murphy & Timbers LLP

(57) ABSTRACT

A cochlear implant includes an active base section with a front surface configured to lie against an inner modiolar wall of the scala tympani. Electrode contacts are on the front surface configured to face the inner modiolar wall to deliver electrode stimulation signals to nearby modiolar neural tissue. A passive apex section has a front surface without electrode contacts configured to lie against an outer lateral wall of the scala tympani. A U-shape transition bend section is at an apical end of the active base section bending in a reverse direction and transitioning into a basal end of the passive apex section such that the back surface of an apical tip of the passive apex section lies adjacent to a back surface of a basal end of the active base section at an electrode opening in the cochlea when the electrode is implanted in the patient.

15 Claims, 7 Drawing Sheets

(56) References Cited

U.S. PATENT DOCUMENTS

| | | | |
|---|---|---|---|
| 6,604,283 B1* | 8/2003 | Kuzma | A61N 1/0541 228/173.4 |
| 7,319,906 B2* | 1/2008 | Kuzma | A61N 1/0541 607/137 |
| 7,720,542 B2* | 5/2010 | Jolly | A61N 1/36032 604/890.1 |
| 7,941,228 B2* | 5/2011 | Kuzma | A61N 1/0541 607/137 |
| 8,280,528 B2* | 10/2012 | Kuzma | A61N 1/0541 607/137 |
| 9,402,990 B2* | 8/2016 | Gibson | A61N 1/0541 |
| 2002/0029074 A1* | 3/2002 | Treaba | A61N 1/0541 607/137 |
| 2004/0225336 A1 | 11/2004 | Milojevic et al. | |
| 2010/0174344 A1 | 7/2010 | Dadd et al. | |
| 2010/0305676 A1* | 12/2010 | Dadd | A61N 1/0541 607/137 |
| 2011/0137393 A1* | 6/2011 | Pawsey | A61N 1/0541 607/137 |
| 2012/0158113 A1* | 6/2012 | Jolly | A61N 1/0541 607/137 |

* cited by examiner

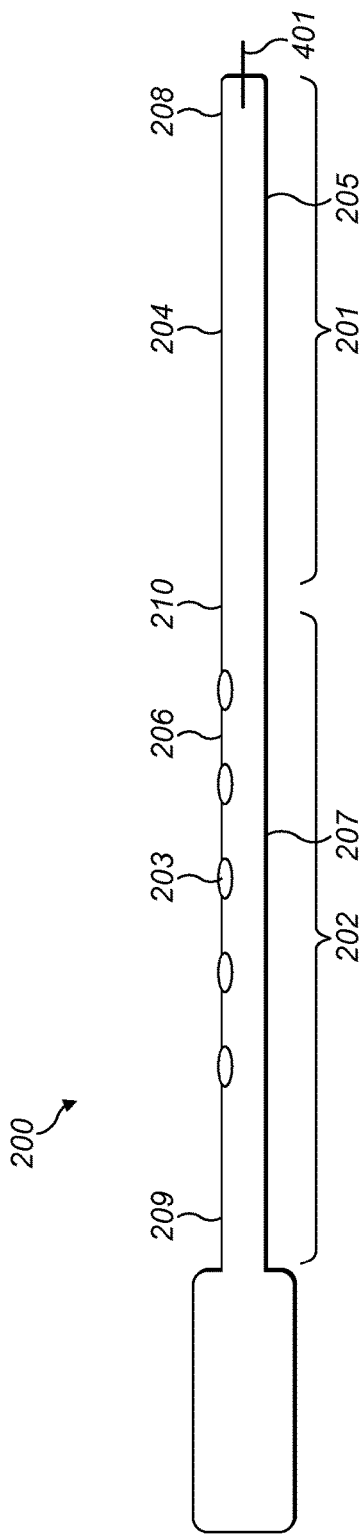
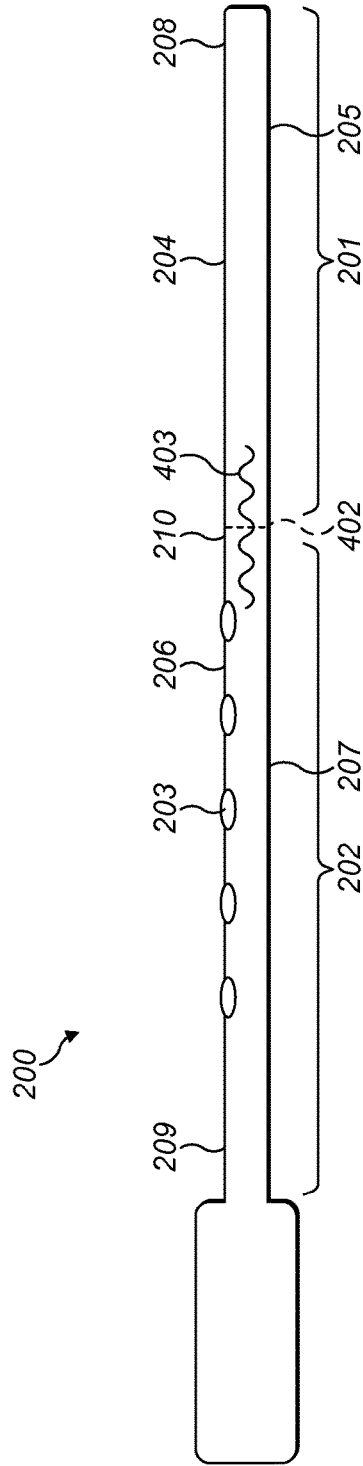
FIG. 4A
FIG. 4B

ATRAUMATIC MODIOLAR HUGGING ELECTRODE

This application claims priority from U.S. Provisional Patent Application 61/808,655, filed Apr. 5, 2013, which is incorporated herein by reference.

FIELD OF THE INVENTION

The present invention relates to an implantable electrode arrangement for cochlear implant systems.

BACKGROUND ART

A normal ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode.

FIG. 1 also shows some components of a typical cochlear implant system where an external microphone provides an audio signal input to an external signal processor 111 in which various signal processing schemes can be implemented. The processed signal is then converted into a digital data format for transmission by external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

The electrode array 110 contains multiple electrode wires embedded in a soft silicone body referred to as the electrode carrier. The electrode array 110 needs to be mechanically robust, and yet flexible and of small size to be inserted into the cochlea 104. The material of the electrode array 110 needs to be soft and flexible in order to minimize trauma to neural structures of the cochlea 104. But an electrode array 110 that is too floppy tends to buckle too easily so that the electrode array 110 cannot be inserted into the cochlea 104 up to the desired insertion depth. A trade-off needs to be made between a certain stiffness of the electrode array 110 which allows insertion into the cochlea 104 up to the desired insertion depth without the array buckling, and certain flexibility of the electrode array 110 which keeps mechanical forces on the structures of the scala tympani of the cochlea 104 low enough.

Recent developments in CI electrode array designs and surgical techniques are moving towards minimal trauma implantations. For preservation of residual hearing it is of particular importance to preserve the natural intra-cochlear structures. Therefore, the size and mechanical characteristics of the electrode array are critical parameters for the best patient benefit. Some electrode array designs are pre-curved, though a drawback of that approach is that a special electrode insertion tool is needed which keeps the electrode array straight until the point of insertion.

As documented by Erixon et al., *Variational Anatomy of the Human Cochlea: Implications for Cochlear Implantation*, Otology & Neurotology, 2008 (incorporated herein by reference), the size, shape, and curvature of the cochlea varies greatly between individuals, meaning that a CI electrode array must match a wide range of scala tympani (ST) geometries. Furthermore, recently published research by Verbist et al., *Anatomic Considerations of Cochlear Morphology and Its Implications for Insertion Trauma in Cochlear Implant Surgery*, Otology & Neurotology, 2009 (incorporated herein by reference) has shown that the human ST does not incline towards the helicotrema at a constant rate, but rather there are several sections along the ST where the slope changes, sometimes even becoming negative (i.e. downwards). The location and grade of these changes in inclination were also found to be different from individual to individual. Consequently, CI electrode arrays should be highly flexible in all directions in order to adapt to individual variations in curvature and changes in inclination of the ST for minimal trauma implantation.

Electrode arrays that lie close to the inner modiolar wall of the cochlear scala tympani are advantageous over the more typical free-fitting electrode arrays that lie against the outer lateral wall in-terms of power consumption and effectiveness in stimulating the spiral ganglion cells of the modiolus. Modiolar hugging electrode arrays known in the prior art are often pre-curved and required a positioning stylet for safe introduce it into the cochlea (e.g., U.S. Pat. No. 5,545,219, U.S. Pat. No. 6,125,302, and U.S. Pat. No. 6,374,143). Other existing perimodiolar hugging electrode arrays require some additional structural elements to ensure placement of the electrode array close to the inner modiolar wall after insertion. However, after insertion there is no opportunity for the surgeon to correct and optimize the position of the electrode array.

U.S. Pat. No. 6,498,954 describes a cochlear implant electrode with a leading section that is attached to the distal end of the electrode array. Two separate cochleostomies are drilled, one at the base and another separate one at the apex of the cochlea. The electrode leading section then is inserted through the basal cochleostomy and advanced towards the apical cochleostomy. A forward end of the leading section is then pulled through the apical cochleostomy which causes the electrode array to be pulled into the cochlea. The leading section must be the leading section must relatively stiff in order to properly move the leading section through the interior of the cochlea from base to apex.

SUMMARY OF THE INVENTION

Embodiments of the present invention are directed to a cochlear implant including an active base section with a front surface configured to lie against an inner modiolar wall of the scala tympani. Electrode contacts are on the front surface configured to face the inner modiolar wall to deliver electrode stimulation signals to nearby modiolar neural tissue. A passive apex section has a front surface without electrode contacts configured to lie against an outer lateral wall of the scala tympani. A U-shape transition bend section is at an apical end of the active base section bending in a reverse direction and transitioning into a basal end of the passive apex section such that the back surface of the passive apex section lies adjacent to a back surface of the active base section when the electrode is implanted in the patient.

The passive apex section may have a thinner cross-section than the active base section; for example, the cross-section of the passive apex section may be half as thick as the cross-section of the active base section. The apical tip of the apex section may be adapted to extend through the electrode opening back to the mastoid bone of the patient.

In some embodiments, there may be a releasable connection between the passive apex section and the active base section adapted to allow the passive apex section to disconnect from the active base section for removal from the scala tympani. In some embodiments, the passive apex section may include an interior volume for holding a therapeutic drug which is released by the electrode into the scala tympani over a treatment period of time. And the apical tip of the apex section may include a fill opening for introducing the therapeutic drug into the interior volume of the passive apex section.

Embodiments of the present invention also include a method of implanting a cochlear implant electrode. An apical tip of a passive apex section of the implant electrode without electrode contacts is anchored at an electrode opening in the cochlea of an implant patient. A U-shape transition bend section is formed in the passive apex section that reverses direction of the passive apex section. The passive apex section is pushed through the electrode opening to advance the transition bend section into the scala tympani of the cochlea with a front surface of the passive apex section facing against an outer lateral wall of the scala tympani and a back surface of the passive apex section facing a center of the scala tympani. The pushing continues to introduce into the scala tympani an active base section of the implant electrode having a back surface facing the center of the scala tympani and a front surface configured to face an inner modiolar wall of the scala tympani, the front surface including electrode contacts for delivering electrode stimulation signals to nearby modiolar neural tissue. The process continues until the active base section is completely within the scala tympani with the back surface of the active base section adjacent to a back surface of the passive apex section.

The passive apex section may have a thinner cross-section than the active base section; for example, the cross-section of the passive apex section may be half as thick as the cross-section of the active base section.

A surgeon implanting the electrode in the cochlea may actively anchor the apical tip of the apex section at the electrode opening. Or the apical tip may include an anchoring pin adapted to be attached at the electrode opening to anchor the apical tip. In addition or alternatively, the apical tip may be anchored to extend back through the electrode opening to the mastoid bone of the patient.

The method may further include introducing a therapeutic drug into an interior volume of the passive apex section for release by the electrode into the scala tympani over a treatment period of time. In addition or alternatively the method may later include disconnecting the passive apex section from the active base section and removing the passive apex section from the scala tympani.

BRIEF DESCRIPTION OF THE DRAWINGS

FIG. 4 A-B illustrates various alternative structural features of an implant electrode according to an embodiment of the present invention.

DETAILED DESCRIPTION OF SPECIFIC EMBODIMENTS

Locating the electrode array close to the modiolar wall is advantageous over conventional free-fitting lateral wall electrode arrays in terms of power consumption and effectiveness in stimulating the spiral ganglion cells. Embodiments of the present invention are directed to a novel and inventive electrode array derived from a lateral wall electrode and having an additional passive part that extends out beyond the apical end. The tip of this passive part is held outside the cochlea and a U-shape bend is created as the active part of the electrode array is pushed into the cochlea. Once the electrode array has been fully inserted, the active part naturally lies close to the modiolar wall and the passive part remains close to the lateral wall side.

Figure 1:
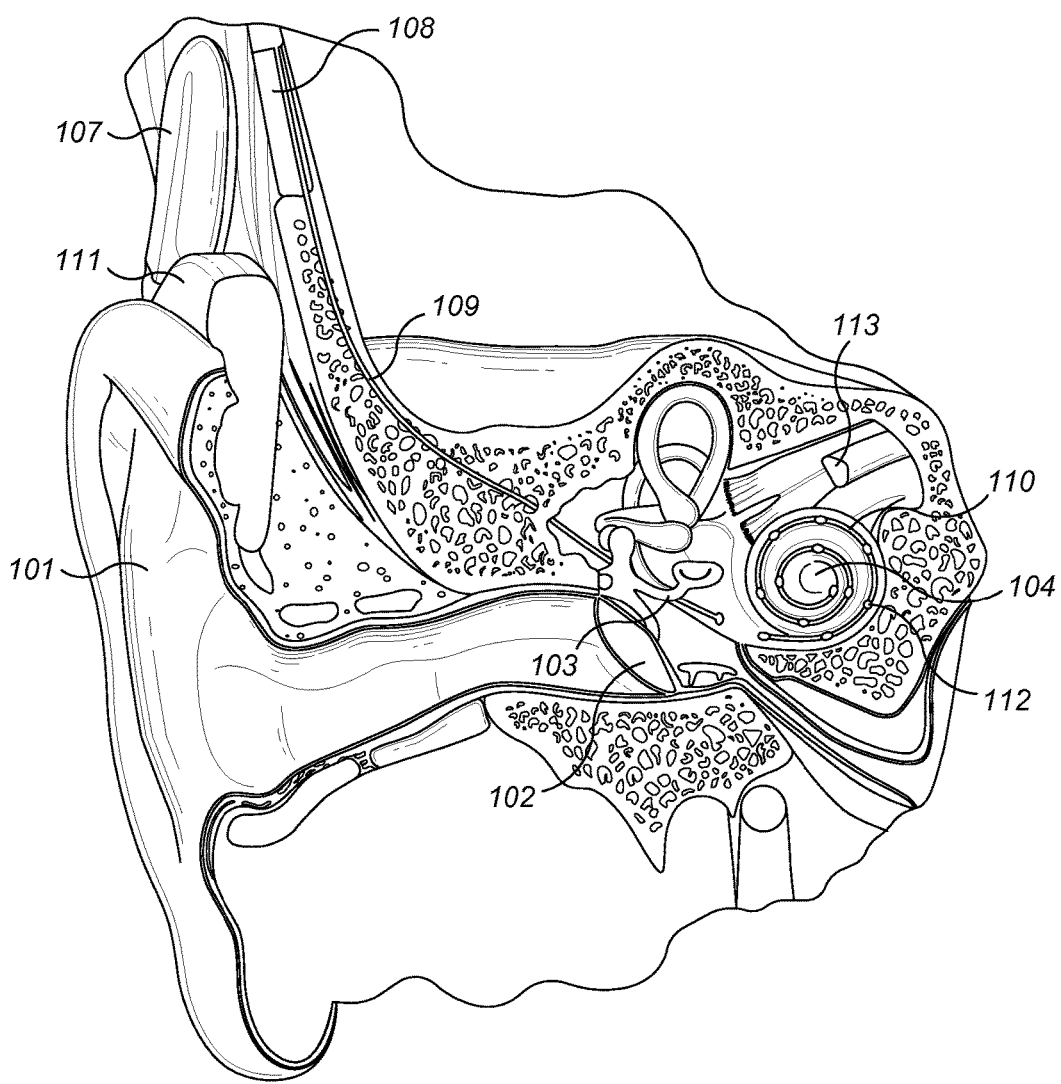
FIG. 1 shows anatomical structures in a human ear having a cochlear implant system.
Figure 2:
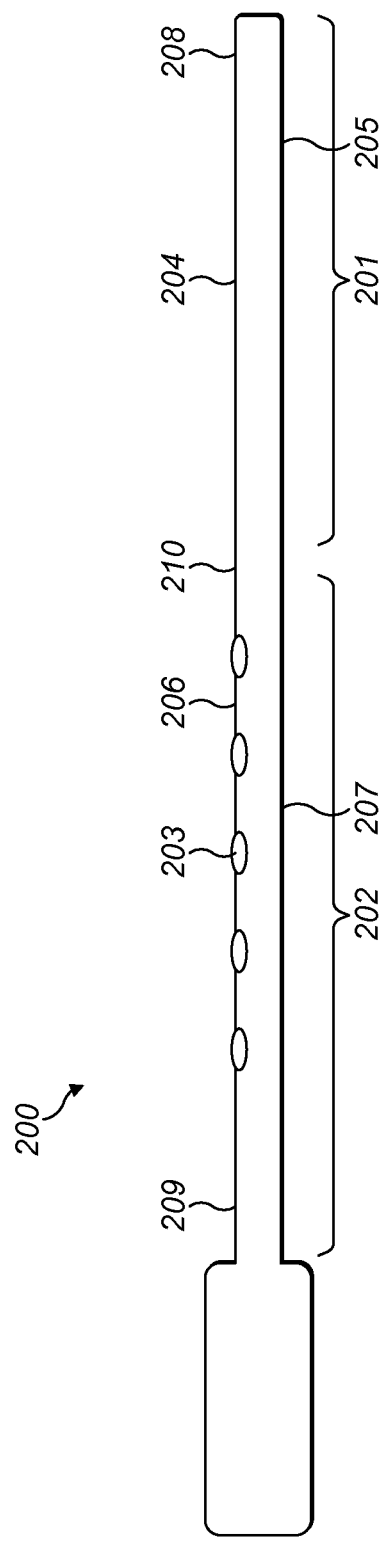
FIG. 2 shows an example of an atraumatic modiolar hugging implant electrode according to one embodiment of the present invention.

FIG. 2 shows an example of an atraumatic modiolar hugging implant electrode 200 which includes an active base section 202 with a front surface 206 configured to lie against an inner modiolar wall of the scala tympani and electrode contacts 203 configured to face the inner modiolar wall to deliver electrode stimulation signals to nearby modiolar neural tissue. A passive apex section 201 has a front surface 204 without electrode contacts configured to lie against an outer lateral wall of the scala tympani. A U-shape transition bend section 210 bends in a reverse direction such that the back surface 205 of the passive apex section 201 lies adjacent to a back surface 207 of the active base section 202 at an electrode opening in the cochlea when the electrode 200 is implanted in the patient. The passive apex section 201 is very flexible in comparison to the active base section 202, both of which may be made of an appropriate medical grade silicone elastomer material. Both sections should be of similar length to achieve full insertion of the active base section 202 to have all the electrode contacts 203 within the cochlea.

Figure 3A:
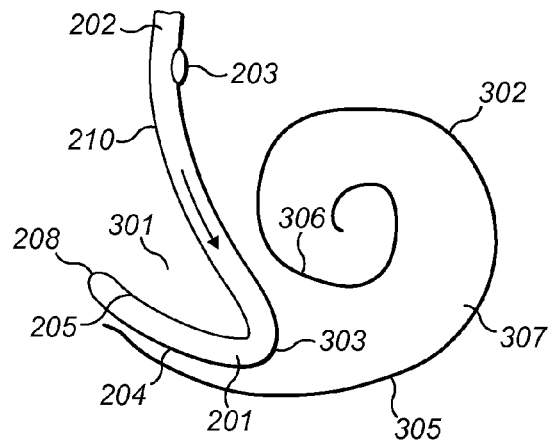
FIG. 3 A-C illustrates the insertion of such an electrode into the scala tympani of an implant patient.
Figure 3B:
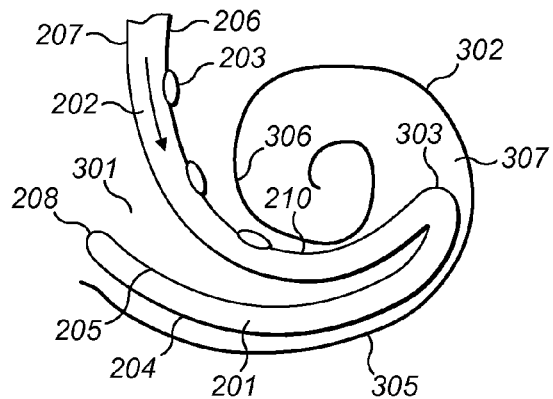
Figure 3C:
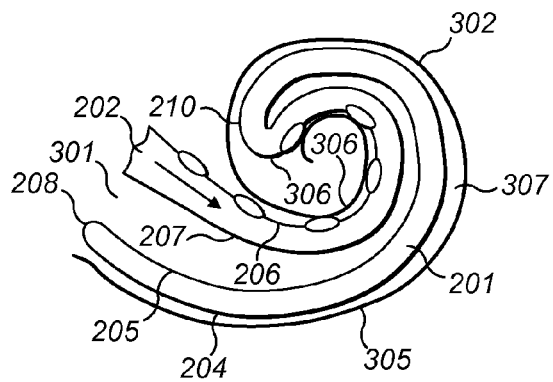

FIG. 3 A-C illustrates the insertion of such an electrode 200 into the scala tympani 307 of an implant patient. As shown in FIG. 3 A, the apical tip 208 is anchored at an electrode opening 301 in the cochlea 302 and a U-shape transition bend section 303 is formed in the passive apex section 201 that reverses direction of the passive apex section 201. The passive apex section 201 is pushed through the electrode opening 301 to advance the transition bend section 303 into the scala tympani 307 with a front surface 204 of the passive apex section 201 facing against an outer lateral wall 305 of the scala tympani 307 and a back surface 205 of the passive apex section 201 facing a center of the scala tympani 307. The pushing continues as shown in FIG. 3 B to introduce into the scala tympani 307 an active base section 202 of the implant electrode 200 having a back surface 210 facing the center of the scala tympani 307 and a front surface 206 configured to face an inner modiolar wall of the scala tympani 307 with the electrode contacts 203 positioned to deliver electrode stimulation signals to nearby modiolar neural tissue. The process continues until the active base section 202 is completely within the scala tympani 307, FIG. 3 C, with the back surface 207 of a basal end 209 of the active base section 202 adjacent to a back surface 205 of the apical tip 208 of the passive apex section 201 at the electrode opening 301.

FIG. 4 A-B illustrates various alternative structural features of an implant electrode 200 according to an embodiment of the present invention. FIG. 4 A shows an anchoring pin 401 at the apical tip 208 which is adapted to be attached at the electrode opening 301 to anchor the apical tip 208 during surgical insertion. Alternatively, a surgeon implanting the electrode 200 in the cochlea 302 may actively anchor the apical tip 208 at the electrode opening 301. In addition or alternatively, the apical tip 208 may be anchored to extend back through the electrode opening 301 to the mastoid bone 701 of the patient (See FIG. 7) or to a surgical insertion guide tool (see, e.g., U.S. 2010/0094311) placed in the middle ear, at the mastoid bone or even externally of the mastoid bone. FIG. 4B shows an implant electrode 200 having an internal bridge wire 403 that connects at a physical section boundary 402 between the passive apical section 201 and the active base section 202 which allows the two sections to be disconnected to remove the passive apex section 201 from the scala tympani 301 after insertion of the active base section 202.

Figure 5:
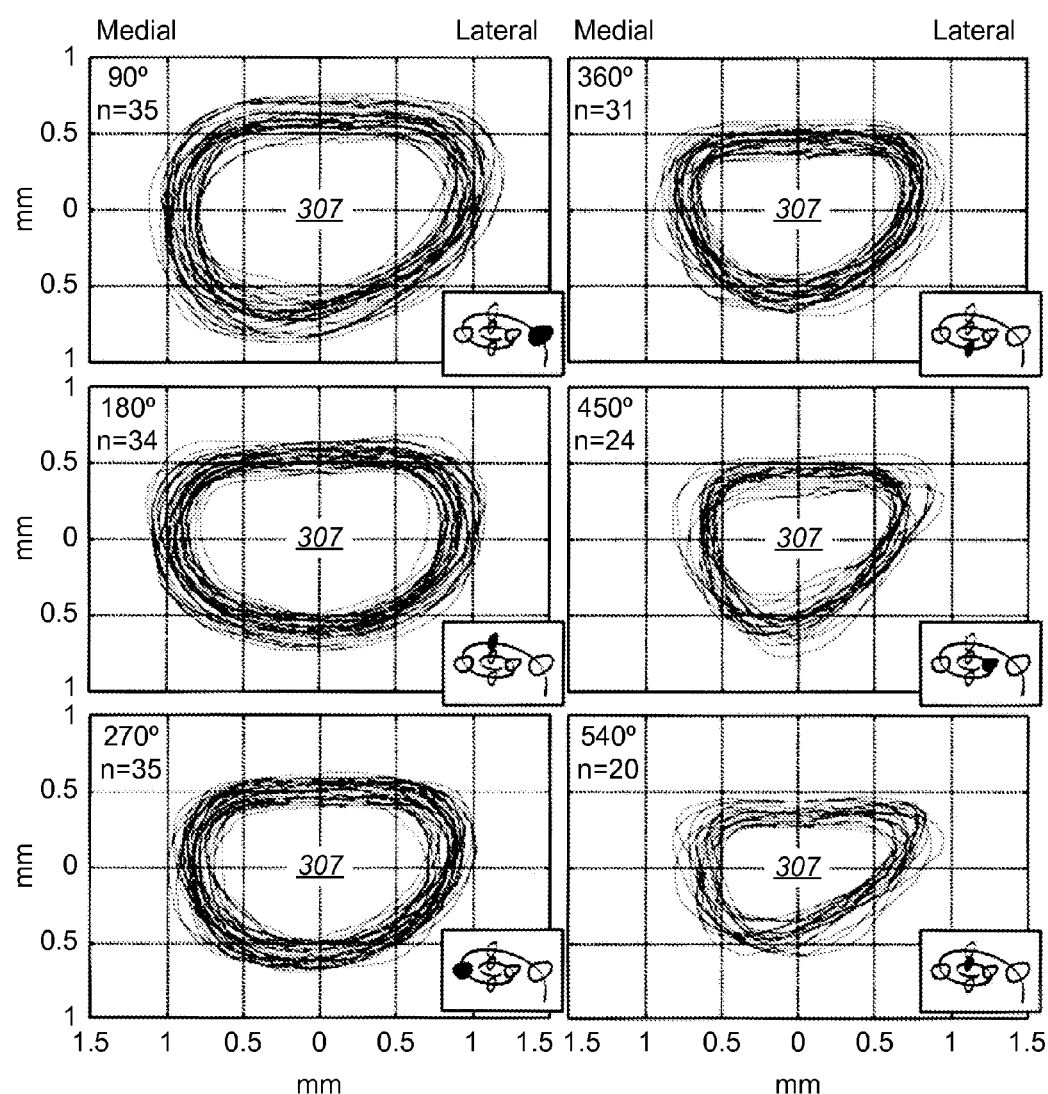
FIG. 5 shows cross-sections of a scala tympani at various rotational locations within a typical cochlea.

FIG. 5 shows cross-sections of a scala tympani 307 at various rotational locations within a typical cochlea. The variations in size and shape at the medial wall on the left side of each cross-section reflects how the front surface 206 of the active base section 202 must be correspondingly adapted in size and shape to fit properly facing the modiolus as closely as possible.

Figure 6A:
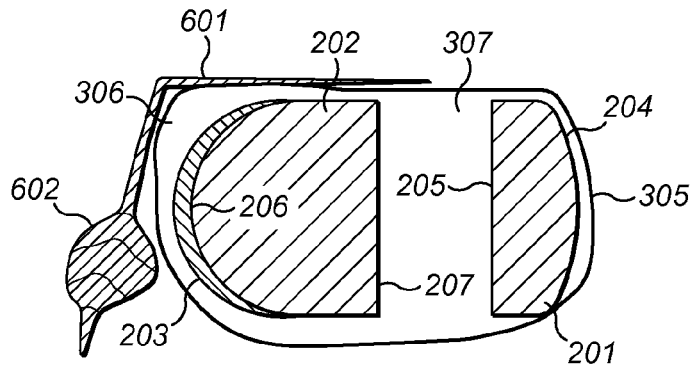
FIG. 6 A-C shows cross-sections of implant electrodes according to embodiments of the present invention.
Figure 6B:
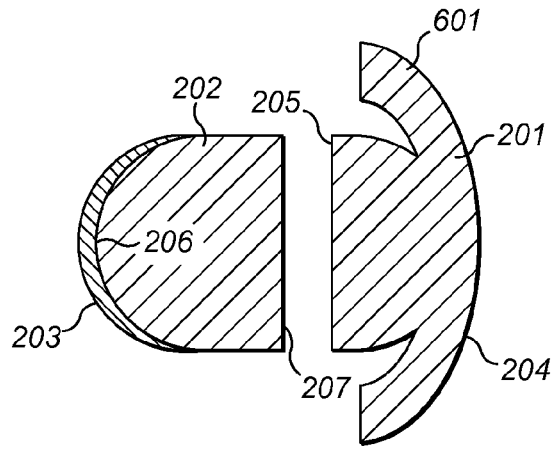
Figure 6C:
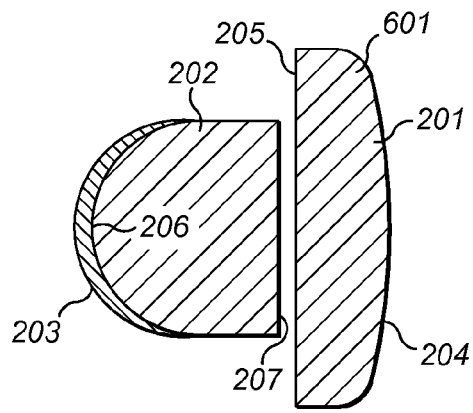

FIG. 6A shows a cross-section of a scala tympani 307 with an implant electrode according to an embodiment of the present invention where the front surface 206 of the active base section 202 configured to face the inner modiolar wall 306 of the scala tympani 307 with the electrode contacts 203 positioned to deliver electrode stimulation signals to nearby modiolar neural tissue 601 connected to the modiolus nerve 602. The front surface 204 of the passive apical section 201 lies against the outer lateral wall 305 of the scala tympani 307 with the back surface 205 facing longitudinal centerline of the scala tympani 207 and the back surface 207 of the active base section 202. FIG. 6 clearly shows the relative thicknesses of the active base section 202 and the significantly thinner passive apical section 201 which only supports insertion of the active base section 202 close to the modiolar wall 306. Typically, the active base section 202 might be twice as thick as the passive apical section 201, but this ratio can vary depending on the specific cross-sectional size of the scala tympani 307 (see FIG. 5). Both the active base section 202 and the passive apical section 201 preferably have an asymmetric form. Both front surface 204 and 206 preferably are curved to lie against the adjacent scala wall, while the respective back surface 205 and 207 are preferably planar to lie next to each other. This asymmetric design helps promote an electrode insertion into the cochlea without twisting the electrode 200.

FIGS. 6 B-C show cross-sections of alternative embodiments wherein the passive apical section 201 includes extended ends 601 that after insertion into the scala tympani 307 act as an electrical shield that minimizes current leakage from the electrode contacts 203 back towards the lateral wall 305. For example, the extended ends 601 may be formed of the same electrically insulating silicone material as the main body of the passive apical section 201.

Figure 7:
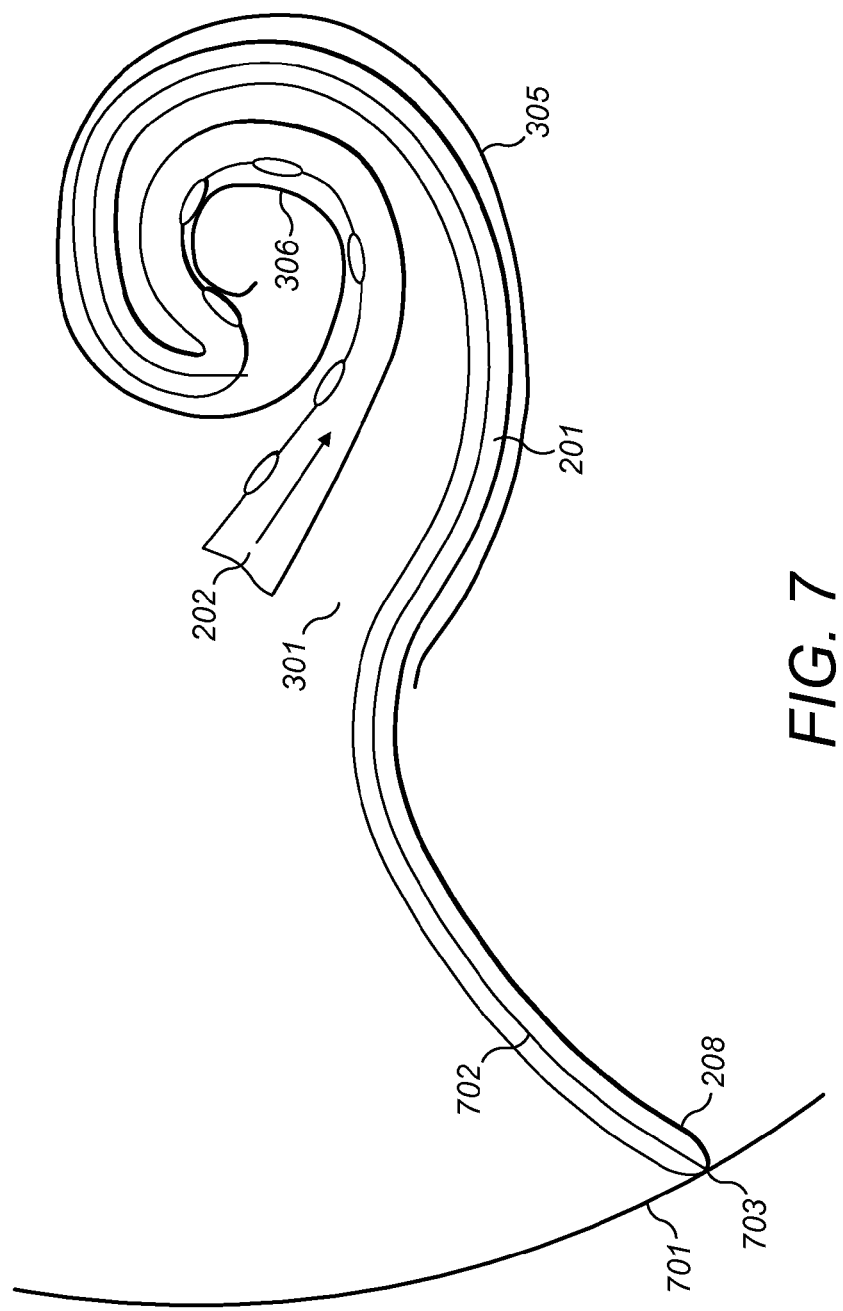
FIG. 7 shows various alternative structural features of an implant electrode according to an embodiment of the present invention.

FIG. 7 shows various alternative structural features of an implant electrode according to an embodiment of the present invention which includes an internal drug delivery channel 702 within the passive apex section 201 for release into the scala tympani 307 over a treatment period of time. A drug fill opening 703 at the apical end 208 at the mastoid bone 701 allows for surgical filling/re-filling of the drug delivery channel 702.

To avoid problems with bacterial infection, after insertion of the active base section, the apical tip of the passive apical section can be cut or pushed inside the scala tympani. Or a fascia piece may be inserted between the back surfaces of the two sections at the electrode opening.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant electrode comprising:
    an active base section with a front surface configured to lie against an inner modiolar wall of a scala tympani in an implanted patient and a back surface facing a center of the scala tympani;
    a plurality of electrode contacts on the front surface of the active base section configured to face the inner modiolar wall to deliver electrode stimulation signals to nearby modiolar neural tissue;
    a passive apex section with a front surface without electrode contacts configured to lie against an outer lateral wall of the scala tympani and a back surface facing the center of the scala tympani; and
    a U-shape transition bend section at an apical end of the active base section bending in a reverse direction and transitioning into a basal end of the passive apex section whereby the back surface of the passive apex section lies adjacent to a back surface of the active base section when the electrode is implanted in the patient.

2. An electrode according to claim 1, wherein the passive apex section has a thinner cross-section than the active base section.

3. An electrode according to claim 2, wherein the cross-section of the passive apex section is half as thick as the cross-section of the active base section.

4. An electrode according to claim 1, wherein an apical tip of the passive apical section is adapted to extend through the electrode opening back to the mastoid bone of the patient.

5. An electrode according to claim 1, further comprising:
    a releasable connection between the passive apex section and the active base section adapted to allow the passive apex section to disconnect from the active base section for removal from the scala tympani.

6. An electrode according to claim 1, wherein the passive apex section includes an interior volume for holding a therapeutic drug and wherein the electrode is adapted to release the therapeutic drug into the scala tympani over a treatment period of time.

7. An electrode according to claim 6, wherein the passive apex section includes a fill opening for introducing the therapeutic drug into the interior volume of the passive apex section.

8. A method of implanting a cochlear implant electrode comprising:

anchoring at an electrode opening in the cochlea of an implant patient an apical tip of a passive apex section of the implant electrode, the passive apex section being without electrode contacts;

forming a U-shape transition bend section in the passive apex section that reverses direction of the passive apex section;

pushing the passive apex section through the electrode opening to advance the transition bend section into the scala tympani of the cochlea with a front surface of the passive apex section facing against an outer lateral wall of the scala tympani and a back surface of the passive apex section facing a center of the scala tympani;

continuing to push through the electrode opening an active base section of the implant electrode having a back surface facing the center of the scala tympani and a front surface configured to face an inner modiolar wall of the scala tympani, the front surface including a plurality of electrode contacts for delivering electrode stimulation signals to nearby modiolar neural tissue, until the active base section is completely within the scala tympani with the back surface of a basal end of the active base section adjacent to a back surface of the apical tip of the passive apex section at the electrode opening.

9. A method according to claim 8, wherein the passive apex section has a thinner cross-section than the active base section.

10. A method according to claim 9, wherein the cross-section of the passive apex section is half as thick as the cross-section of the active base section.

11. A method according to claim 8, wherein a surgeon implanting the electrode in the cochlea actively anchors the apical tip at the electrode opening.

12. A method according to claim 8, wherein the apical tip includes an anchoring pin adapted to be attached at the electrode opening to anchor the apical tip.

13. A method according to claim 8, wherein the apical tip is anchored to extend back through the electrode opening to the mastoid bone of the patient.

14. A method according to claim 8, further comprising:
introducing a therapeutic drug into an interior volume of the passive apex section for release by the electrode into the scala tympani over a treatment period of time.

15. A method according to claim 8, further comprising:
disconnecting the passive apex section from the active base section; and
removing the passive apex section from the scala tympani.

* * * * *